(12) United States Patent
Kawai et al.

(10) Patent No.: US 9,132,456 B2
(45) Date of Patent: Sep. 15, 2015

(54) CLEANING METHOD FOR A WORKING MECHANISM FOR MEDICAL MANIPULATOR

(71) Applicant: Karl Storz GmbH & Co. KG, Tuttlingen (DE)

(72) Inventors: Junko Kawai, Tokyo (JP); Makoto Jinno, Shizuoka (JP)

(73) Assignee: Karl Storz GmbH & Co. KG (DE)

( * ) Notice: Subject to any disclaimer, the term of this patent is extended or adjusted under 35 U.S.C. 154(b) by 0 days.

(21) Appl. No.: 14/317,666

(22) Filed: Jun. 27, 2014

(65) Prior Publication Data

US 2014/0305472 A1    Oct. 16, 2014

Related U.S. Application Data

(62) Division of application No. 12/175,556, filed on Jul. 18, 2008, now Pat. No. 8,795,324.

(30) Foreign Application Priority Data

Jul. 30, 2007    (JP) ................................. 2007-197582

(51) Int. Cl.
*A61B 17/00*    (2006.01)
*B08B 3/04*    (2006.01)
*A61B 17/29*    (2006.01)
*A61B 19/00*    (2006.01)

(52) U.S. Cl.
CPC . *B08B 3/04* (2013.01); *A61B 17/29* (2013.01); *A61B 17/2909* (2013.01); *A61B 19/34* (2013.01); *A61B 19/2203* (2013.01); *A61B 2017/0046* (2013.01); *A61B 2017/00398* (2013.01); *A61B 2017/00477* (2013.01); *A61B 2017/2912* (2013.01); *A61B 2017/2925* (2013.01); *A61B 2017/2929* (2013.01); *A61B 2017/2934* (2013.01); *A61B 2019/2223* (2013.01); *A61B 2019/2234* (2013.01); *A61B 2019/2242* (2013.01); *A61B 2019/2276* (2013.01); *A61B 2019/343* (2013.01); *Y10T 74/20305* (2015.01)

(58) Field of Classification Search
CPC ..................................................... A61B 17/00
See application file for complete search history.

(56) References Cited

U.S. PATENT DOCUMENTS

| | | | |
|---|---|---|---|
| 5,312,023 | A | 5/1994 | Green et al. |
| 5,904,690 | A | 5/1999 | Middleman et al. |
| 7,314,473 | B2 | 1/2008 | Jinno et al. |
| 2004/0118440 | A1 | 6/2004 | Sasaki et al. |
| 2006/0025812 | A1 | 2/2006 | Shelton, IV |

FOREIGN PATENT DOCUMENTS

| | | |
|---|---|---|
| JP | 2004105283 A | 4/2004 |
| JP | 2004105451 A | 4/2004 |

*Primary Examiner* — Benjamin Packard
(74) *Attorney, Agent, or Firm* — Whitmyer IP Group LLC

(57) ABSTRACT

A cleaning method for a working mechanism for a medical manipulator, the working mechanism including a shaft, a force transmitting member in the shaft, a working unit at one end of the shaft with a working unit moved by the force transmitting member, and a cover over a portion of the working unit, with a gap between the cover and shaft, and a hole is disposed on a side of the cover. The method includes the steps of inserting an end of the shaft with the cover into one end of a tube, sealing the tube and shaft with a sealing element, disposing a sucking and discharging element on another end of the tube, and immersing another end of the shaft into a cleaning agent. By activating the sucking and discharging element, sucking and discharging of the cleaning agent is carried out repeatedly, from the other end of the shaft.

17 Claims, 9 Drawing Sheets

CLEANING METHOD FOR A WORKING MECHANISM FOR MEDICAL MANIPULATOR

FIELD OF THE INVENTION

The present invention relates to a working mechanism for a medical manipulator and a cleaning method therefor, and in particular, concerns a medical manipulator working mechanism, which can be applied to the working unit of a manipulator equipped with a driving unit and a working unit that is attachable and detachable with respect to the driving unit. The present invention also concerns a cleaning method utilized on such a working mechanism.

BACKGROUND OF THE INVENTION

In laparoscopic surgery, a number of small holes are opened in a patient's abdomen or the like, and an endoscope, a forceps (or manipulator) or the like is inserted, and surgery is carried out while the surgeon observes an image from the endoscope on a monitor. In this type of laparoscopic surgery, owing to the fact that opening of the abdominal cavity is unnecessary, the burden on the patient is small, and the number of days required for the post-operative recovery and the number of days spent in the hospital can be significantly reduced. Therefore, laparoscopic surgical operations are expected to find an increased range of applications.

A manipulator system, for example, as disclosed in Japanese Laid-Open Patent Publication No. 2004-105451, comprises a manipulator main body, and a controller for controlling the main body. The manipulator main body comprises an operation command unit, which is operable by hand, and a working unit, which is detachable and exchangeable with respect to the operation command unit.

The working unit (tool) includes an elongate connecting shaft, and a distal end working unit (also referred to as an "end effector") disposed at the end of the connecting shaft. One or more actuators (motors) are disposed in an operation command unit for driving the working unit by means of wires. The wires are wound around pulleys at a proximal end side. The controller drives the motors disposed in the operation command unit, and also drives the wires in an advancing/retracting manner via the pulleys.

The working unit is constructed so as to be detachable with respect to the operation command unit in order to enable cleaning to be carried out easily following completion of a surgical technique. Further, in laparoscopic surgery, various different types of working units are used depending on the surgery involved. A gripper, scissors, an electrical knife, an ultrasonic knife, a surgical drill or the like may be given as examples thereof. From the standpoint of being able to exchange these working units, a structure in which the working unit is detachable with respect to the operation command unit also is beneficial.

In the working unit, proximal end side pulleys thereof are constructed so as to engage with the rotational shafts of motors, which are disposed in the operation command unit.

By detaching and removing the working unit from the operation command unit, cleaning processing performed on the working unit becomes considerably easier. However, it would also be desirable for cleaning of the mechanisms, such as pulleys and gears or the like, which are disposed within the proximal end side, and in the distal end working unit (end effector) part of the working unit, to be conducted more easily.

The pulleys and gears are connected by wires within the working unit, whereby motive forces are transmitted thereby. It is desired to easily and reliably transmit motive forces through such pulleys, gears, and wires.

SUMMARY OF THE INVENTION

It is one of the objects of the present invention to provide a working mechanism for a medical manipulator, which is highly suitable and effective when applied to the manipulator and to provide a cleaning method for such a working mechanism.

According to one aspect of the present invention, a working mechanism for a medical manipulator includes a hollow shaft, a motive force transmitting member disposed in the shaft, a working unit disposed on one end of the shaft and equipped with a distal end working unit, which is moved by the motive force transmitting member, and a cover that covers at least a portion of the distal end working unit, wherein a gap is provided between the cover and the shaft, and holes are disposed laterally on sides of the cover.

Owing to the presence of the cover, foreign matter can be prevented from entering into the working unit. Also, a cleaning agent may be made to flow through the holes from sides of the cover, or a cleaning means may be inserted through the holes, thereby carrying out cleaning of the working unit.

According to another aspect of the present invention, in the cleaning method, when cleaning of the working mechanism is carried out, an end of the shaft is inserted together with the cover into one end of a tube, the tube and the shaft are sealed by a sealing means, a cleaning agent sucking and discharging means is disposed on another end of the tube, and another end of the shaft is immersed into the cleaning agent. Thus, by activating the sucking and discharging means, sucking and discharging of the cleaning agent is carried out repeatedly from the other end of the shaft.

Owing thereto, the cleaning agent can be sucked and discharged through the hollow space inside the shaft, the cleaning agent is not blocked by the pulleys, gears, and the like of the distal end working unit, and cleaning can be performed easily and effectively by causing the cleaning agent to flow through the gap and the holes.

The above and other objects features and advantages of the present invention will become more apparent from the following description when taken in conjunction with the accompanying drawings, in which a preferred embodiment of the present invention is shown by way of illustrative example.

DETAILED DESCRIPTION OF THE INVENTION

Descriptions of an embodiment of a working mechanism for a medical manipulator and a cleaning method therefor, utilizing the medical manipulator according to the present invention, shall be described below with reference to FIGS. 1 through 9.

The medical manipulator 10 grips a portion of a living body or a curved needle or the like by a distal end working unit 12 to carry out predetermined processing, and ordinarily is referred to as a gripping forceps or a needle driver (needle holder) or the like.

Figure 1:
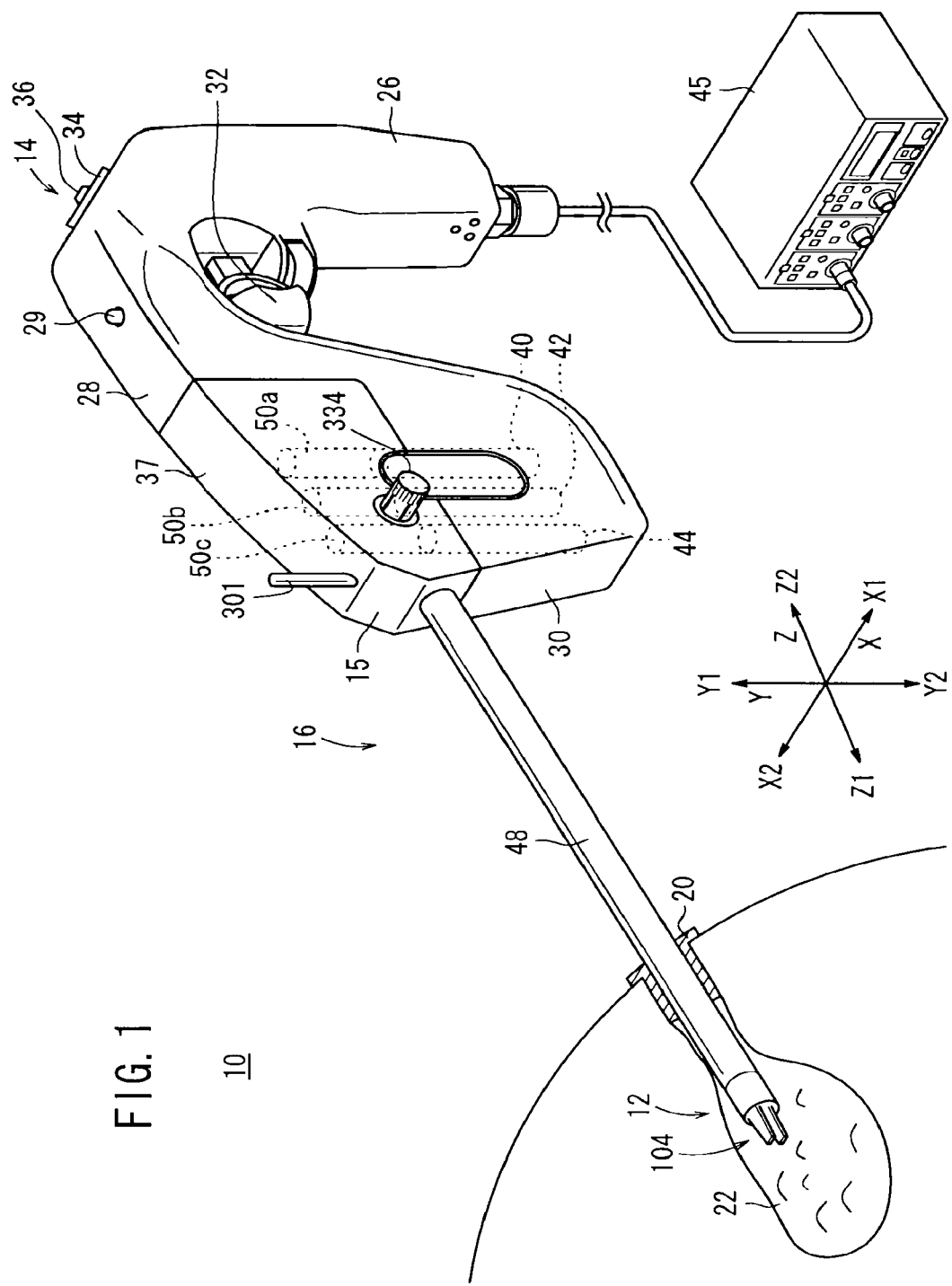
FIG. 1 is a perspective view of a manipulator according to an embodiment of the present invention.
Figure 2:
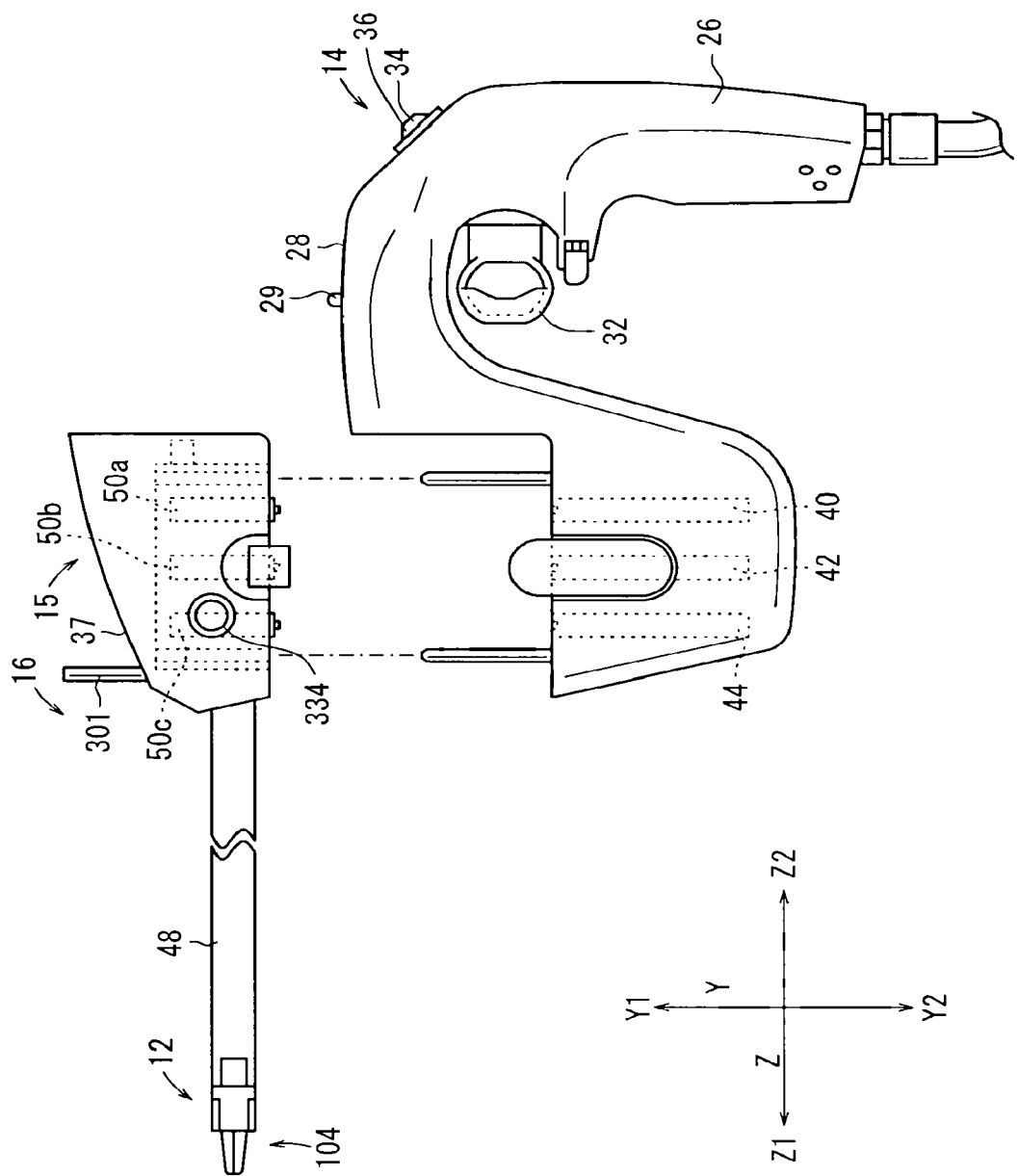
FIG. 2 is a side plan view of the manipulator, in which the working unit and an operation command unit thereof are separated from each other.

As shown in FIGS. 1 and 2, the manipulator 10 includes an operation command unit (driving unit) 14 at a proximal end portion thereof, which is gripped and operated by hand, and a working unit (medical manipulator working mechanism) 16 that is attachable and detachable with respect to the operation command unit 14.

It shall be assumed in the following descriptions that, as shown in FIG. 1, the transverse direction is defined as an X direction, the vertical direction as a Y direction, and the longitudinal directions of the connecting shaft 48 as a Z direction. Further, among the X directions, the rightward direction is defined as an X1 direction, and the leftward direction as an X2 direction, among the Y directions, the upward direction is defined as a Y1 direction, and the downward direction as a Y2 direction, and among the Z directions, the forward direction is defined as a Z1 direction, and the rearward direction as a Z2 direction. Moreover, unless otherwise noted, these directions represent directions of the manipulator 10 when it is in a neutral posture (the posture of the state shown in FIG. 3). The definitions of the above directions are for illustrative purposes only, and the manipulator 10 can be used in any of various orientations (for example, the manipulator may be used upside down).

The working unit 16 includes a distal end working unit 12, a connector (retaining chamber) 15 that is connected to an actuator block 30 of the operation command unit 14, and a hollow connecting shaft 48 of a given length dimension connected between the distal end working unit 12 and the connector 15. The working unit 16 is capable of being detached and separated from the operation command unit 14 by means of a predetermined operation in the actuator block 30, wherein cleaning, disinfecting or sterilizing, maintenance and the like can be carried out thereon.

The distal end working unit 12 and the connecting shaft 48 are narrow in diameter, and can be inserted into a body cavity 22 through a trocar 20 in the form of a hollow cylinder mounted in an abdominal region or the like of the patient. By operations of the operation command unit 14, various techniques can be performed to cut, grip, remove, suture, or ligate (tie-knot) an affected part of the patient's body within the body cavity 22.

The operation command unit 14 includes a grip handle 26, which is gripped by hand, a bridge 28 extending from an upper portion of the grip handle 26, and the actuator block 30, which is connected to a distal (frontal) end of the bridge 28.

As understood clearly from FIG. 1, a lower surface of the connector 15 abuts against an upper surface of the actuator block 30 with substantially no gaps therebetween, whereas the rear surface (surface facing the Z2 direction) of the connector 15 abuts against a front surface (surface facing the Z1 direction) of the bridge 28 with substantially no gaps therebetween. The lower surface of the connector 15 and the upper surface of the actuator block 30 lie in the XZ plane, and the rear surface of the connector 15 and the front surface of the bridge 28 lie in the XY plane. The left and right side surfaces of the connector 15 and the left and right side surfaces of the bridge 28 and the actuator block 30 make up a continuous YZ plane respectively, whereas the upper surface of the connector 15 and the upper surface of the bridge 28 respectively and continuously form a smooth curved surface. Owing thereto, the connector 15 is formed integrally and compactly with respect to the operation command unit 14, and moreover, since unnecessary irregularities in shape hardly exist at the region where the connector 15 and the operation command unit 14 are interconnected, operability is excellent.

The grip handle 26 includes a trigger lever 32, which is operable by a finger of the user, a first command lever 34, and a second command lever 36. The trigger lever 32 is disposed in a position where it can easily be pulled by the index finger.

The actuator block 30 houses therein three motors 40, 42, 44 (actuators) corresponding to respective mechanisms providing three degrees of freedom, which are incorporated in the distal end working unit 12. The motors 40, 42, 44 are arrayed in parallel in the longitudinal direction of the connecting shaft 48. The motors 40, 42, 44 are small in size and narrow in diameter, thereby allowing the actuator block 30 to have a compact flat shape. The actuator block 30 is disposed downwardly of the end of the operation command unit 14 in the Z1 direction. The motors 40, 42, 44 are energized to rotate drive shafts thereof under the control of a controller (control unit) 45, based on operations of the operation command unit 14.

The connector 15 is covered by a resin cover 37, and houses and retains rotatably therein driven pulleys (driven rotating bodies) 50a, 50b, 50c, which engage with drive axes of the motors 40, 42, 44. Wires (linear bodies) 52, 54, 56 are wound respectively around pulleys 50a, 50b, 50c, extending to the distal end working unit 12 through a hollow space 48a (see FIG. 3) of the connecting shaft 48. The wires 52, 54, 56 can be formed of the same type of materials having the same diameter, respectively.

The wires 52, 54, 56 serve to transmit motive forces to a compound mechanism 102 and the end effector 104 through a wire coupling 100 (see FIG. 3) at the end of the connecting shaft 48.

Further, between the cover 160 and the connecting shaft 48, a gap 51 is provided through which a gear 134, and another gear 138, etc., are exposed. The gap 51 communicates with the hollow space 48a of the connecting shaft 48.

A pair of tongue-members 58, which project at the distal end of the connecting shaft 48, are disposed so as to face one another toward the central axis of the connecting shaft 48. The hollow space 48a of the connecting shaft 48 communicates with the space formed between the pair of tongue-members 58. Two pairs of respective shaft holes 60a, 60a and 60b, 60b are disposed in confronting positions in the pair of tongue-members 58. The distal ends of the tongue-members 58 are formed with arcuate shapes, respectively. Further, confronting inside surfaces of the tongue-members 58 are formed as parallel flat surfaces.

The two shaft holes 60a, 60a and the two shaft holes 60b, 60b are disposed so as to sandwich the central axis therebetween. The shaft holes 60a and 60b are disposed in parallel along the Z direction, with the shaft holes 60b being positioned more closely to the distal end side than the shaft holes 60a.

Figure 3:
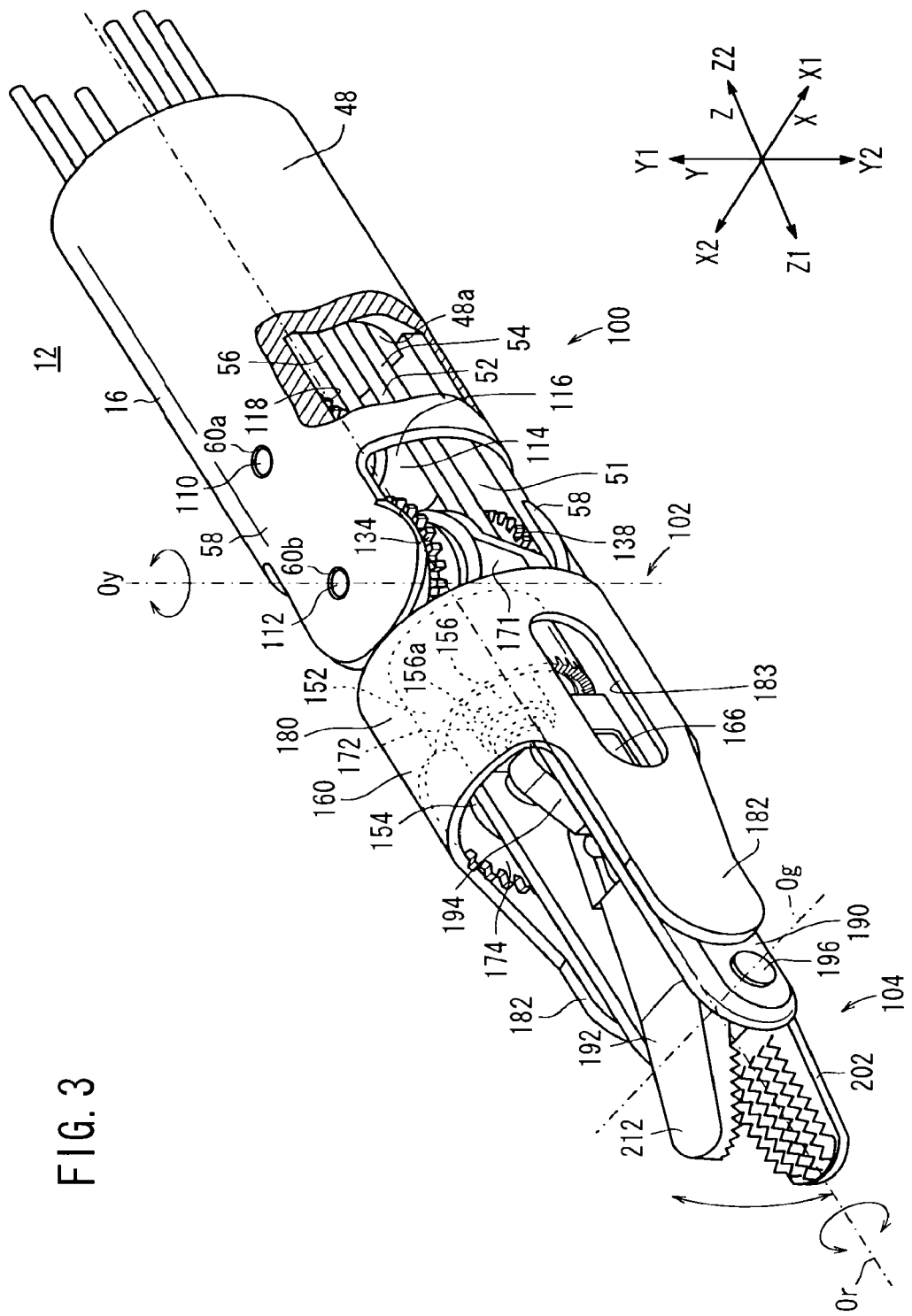
FIG. 3 is a perspective view of a distal end working unit in the manipulator according to the present embodiment.
Figure 4:
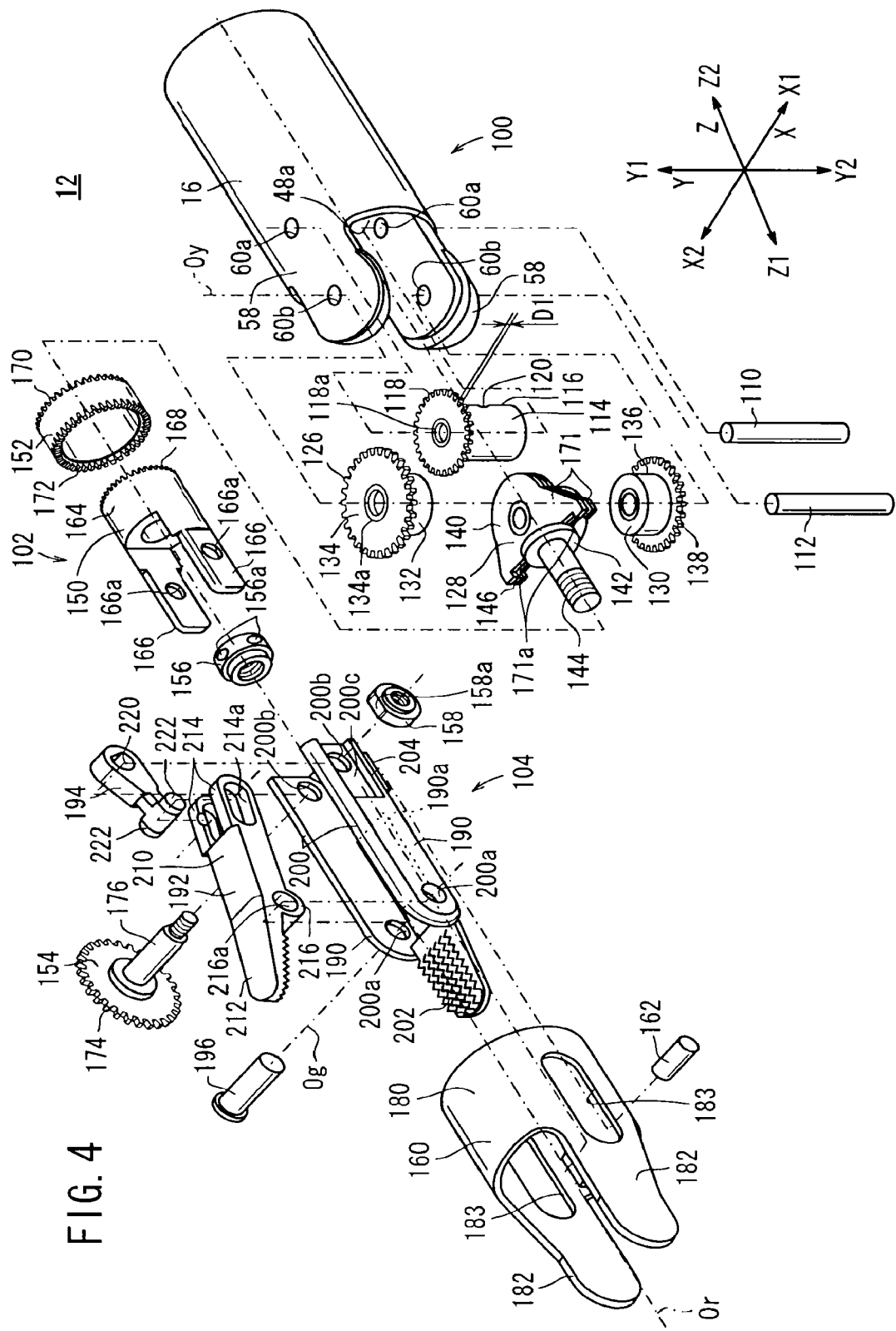
FIG. 4 is an exploded perspective view of the distal end working unit in the manipulator according to the present embodiment.

As shown in FIG. 3, the distal end working unit 12 incorporates therein mechanisms providing three degrees of freedom. These mechanisms include a mechanism having a first degree of freedom for rotating an end portion that is positioned ahead of a first rotational axis Oy (pivot axis) extending along the Y-axis direction, in yawing directions about the first rotational axis Oy, a mechanism having a second degree of freedom for rotating the end portion in rolling directions about a second rotational axis Or, and a mechanism having a third degree of freedom for opening and closing the end effector 104 about a third rotational axis Og.

The end effector 104 makes up a portion for performing actual work during an operation. The first rotational axis Oy and the second rotational axis Or serve to change the posture of the end effector 104 to facilitate working. In general, the mechanism having the third degree of freedom for opening and closing the end effector 104 is referred to as a gripper. The mechanism having the first degree of freedom for rotating in yawing directions is referred to as a yaw axis, whereas the mechanism having the second degree of freedom for rotating in rolling directions is referred to as a roll axis.

The distal end working unit 12 is made up of and includes the wire coupling 100, the compound mechanism 102, and the end effector 104.

With reference to FIGS. 3, 4, 5 and 6, detailed explanations shall now be made concerning the wire coupling 100, the compound mechanism 102, and the end effector 104.

The wire coupling 100 is disposed between the pair of tongue-members 58, and serves to convert reciprocating motions of the respective wires 52, 54, 56 into rotary motions, which are then transmitted to the compound mechanism 102. The wire coupling 100 includes a shaft 110 inserted through the shaft holes 60a, 60a, another shaft 112 (perpendicular shaft) inserted through the shaft holes 60b, 60b, and a gear body 114, which is axially and rotatably supported about the shaft 110. The shafts 110 and 112 are fixed by press fitting or welding, for example, with respect to the shaft holes 60a, 60b. The shaft 112 is positioned on the first rotational axis Oy.

The gear body 114 comprises a tubular body 116 and a gear 118 disposed concentrically on an upper portion of the tubular body 116. The gear 118 comprises a spur gear greater in diameter than the tubular body 116. Unless otherwise specified, the gears referred to herein comprise spur gears. The gear body 114 has a height, which is substantially equal to the distance H, and is rotatably disposed between the pair of tongue-members 58. The gear 118 has a thickness D1 sufficiently thinner than the height H, so that the height (H−D1) of the tubular body 116 takes up a substantial portion of the height H between the tongue-members 58. The gear 118 has a low annular rib 118a disposed on an upper surface thereof around the hole through which the shaft 110 is inserted. The annular rib 118a prevents the upper surface of the gear 118 from contacting the upper tongue-member 58, thereby reducing sliding resistance therebetween.

The compound mechanism 102 is a mechanism that serves both to open and close the end effector 104, as well as to, in combination therewith, cause a change in the posture of the end effector 104.

The compound mechanism 102 comprises a gear body 126, a main axis member 128, and a gear body 130, which are rotatably supported on the shaft 112, and are arranged successively from the Y1 direction toward the Y2 direction.

The gear body 126 comprises a tubular body 132 and a gear 134 disposed concentrically on an upper portion of the tubular body 132. The gear 134 meshes with the gear 118 and has the same thickness as the gear 118. The gear 134 has a greater number of gear teeth than the gear 118 and can transmit rotation of the gear 118 at a reduced speed (while increasing torque). Naturally, depending on design conditions, rotation may also be transmitted at the same speed or at a higher speed. The gear 134 has a low annular rib 134a disposed on the upper surface thereof around the hole through which the shaft 112 is inserted. The annular rib 134a prevents the upper surface of the gear 134 from contacting the upper tongue-member 58, thereby reducing sliding resistance therebetween.

The gear body 130 is essentially identical in shape to the gear body 126, but is in an upside-down orientation with respect to the gear body 126. The gear body 130 comprises a tubular body 136 and a gear 138 disposed concentrically on a lower portion of the tubular body 136. The tubular body 136 is substantially identical in diameter and shape to the tubular body 132. The gear 138 has a number of teeth, which may be somewhat smaller than that of the teeth of the gear 134. A wire securing mechanism 120, which is similar to the wire securing mechanism 120 of the tubular body 116, is disposed on a side surface of the tubular body 136 that faces the Z2 direction, such that the wire 54 is fastened to the tubular body 136 thereby.

The main axis member 128 has a tubular body 140 through which the shaft 112 is inserted, an annular seat 142 facing the Z1 direction, and a support bar 144 extending from the center of the annular seat 142 in the Z1 direction. The support bar 144 is aligned axially with the second rotational axis Or. The support bar 144 has an externally threaded distal end portion.

The annular seat 142 is disposed at a position spaced slightly from the outside surface of the tubular body 140 through two upper and lower protective plates 171, and a hole 146 through which the wire 52 can be inserted is disposed between the tubular body 140 and the annular seat 142. On a side surface in the Z2 direction of the tubular body 140, a wire securing mechanism 120, which is the same as that of the tubular body 116, is provided, to which the wire 52 is fixed.

The protective plate 171 has a roughly 90° circular arc shape in the Z2 direction, expands in the Z1 direction, and is substantially in the shape of a chevron when viewed in plan.

Figure 5:
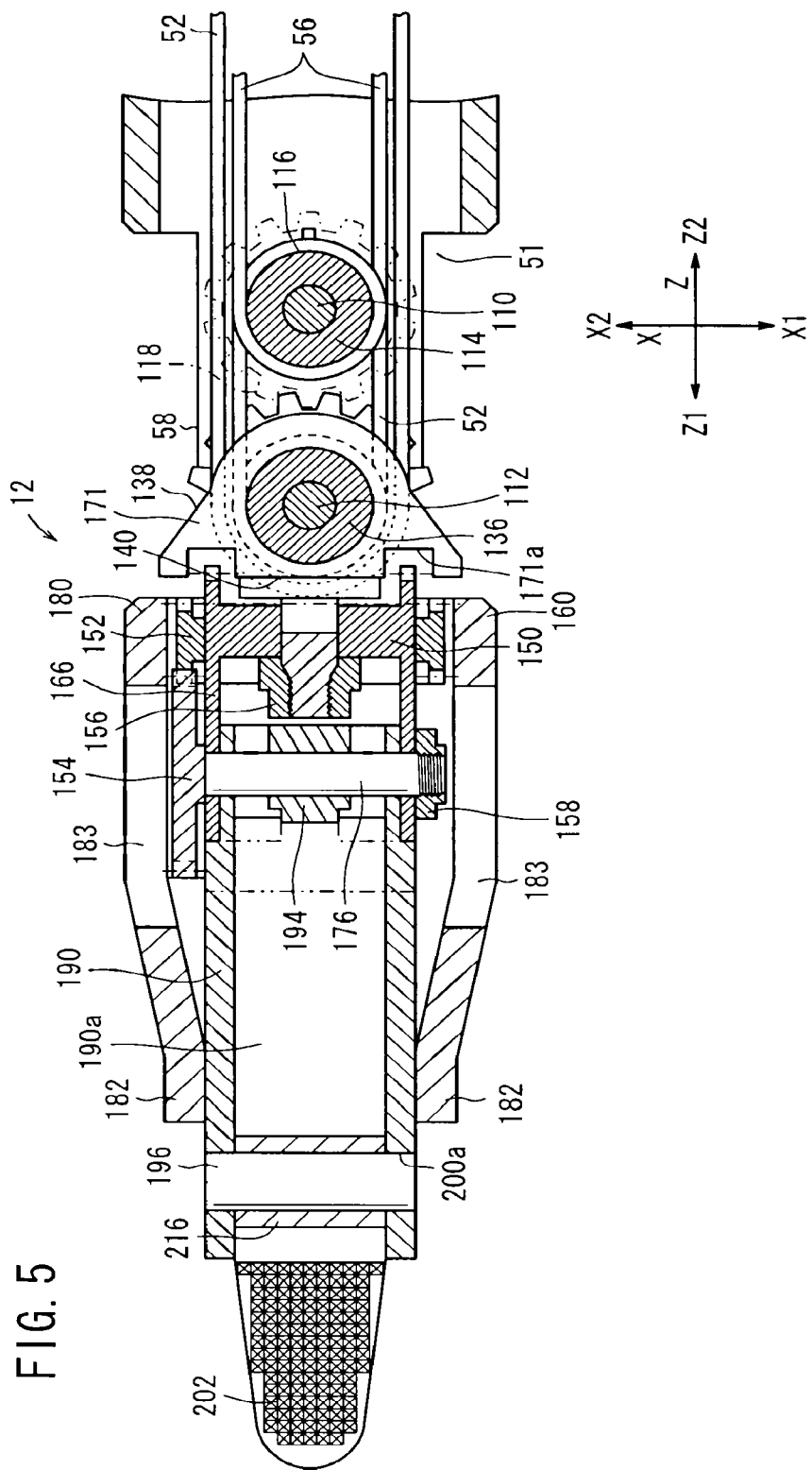
FIG. 5 is a cross sectional top plan view of the distal end working unit in the manipulator according to the present embodiment.
Figure 6:
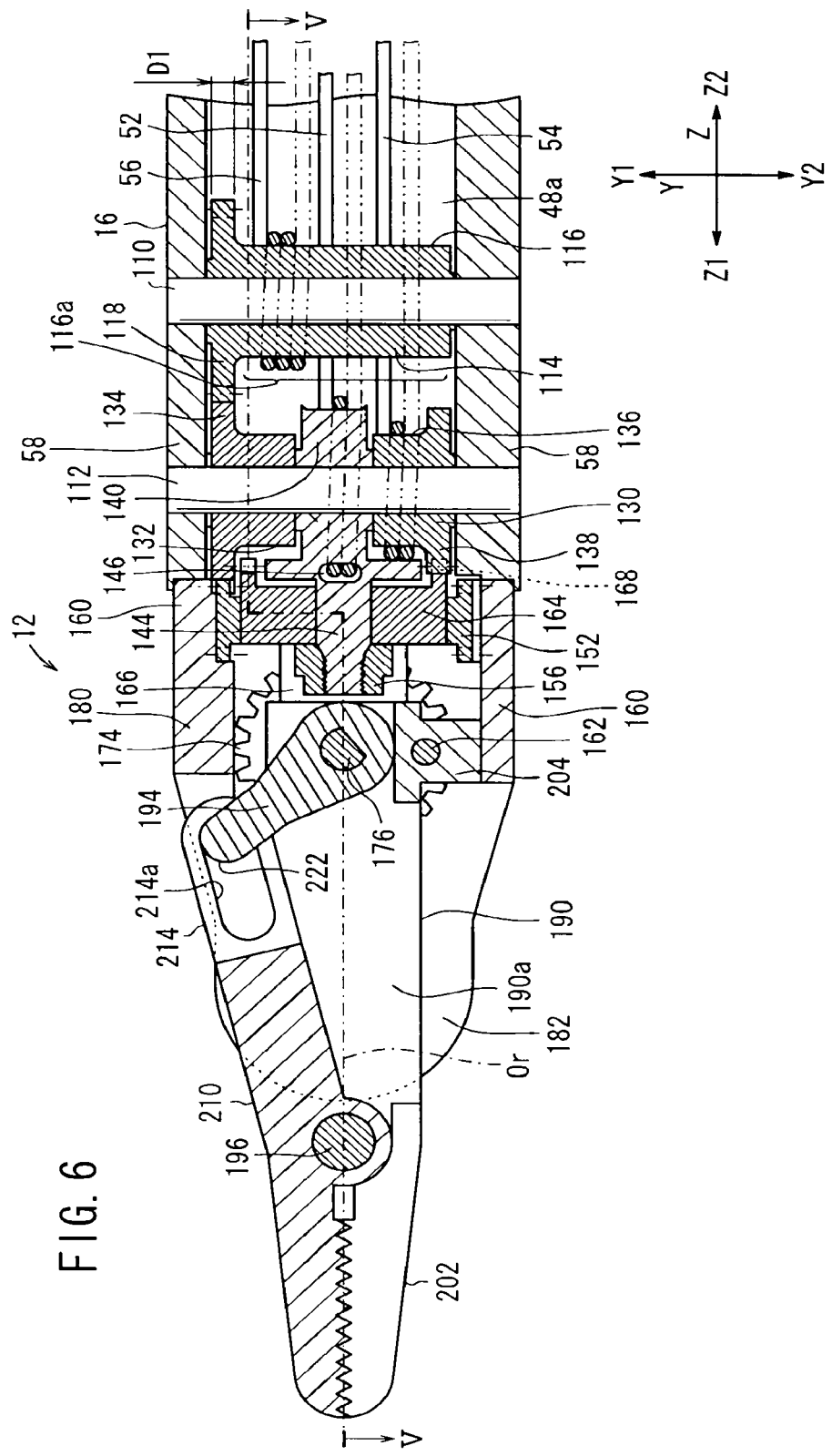
FIG. 6 is a cross sectional side view of the distal end working unit in the manipulator according to the present embodiment.

As shown in FIG. 5, when viewed in plan, the maximum width of the protective plate 171 is wider than the gear 118, the gear 134, and the gear 138. Further, the teeth of the face gear 168 and the face gear 170 are inserted into a recess 171a provided in the end surface facing the Z1 direction. Accordingly, the gear teeth do not come into contact with a suture (thread) or the like that is used for performing a ligation (tie-knot) operation, and sutures are not drawn therein, so that entanglement or interference with the gear teeth can be prevented.

It is not essential that the protective plate 171, which acts as a member for preventing entanglement or interference of threads, etc., be constructed integrally with the main axis member 128. For example, the protective plate 171 may be disposed separately from the main axis member 128 and underneath the main axis member 128 (in the Y2 direction).

In this manner, as a result of the protective plate 171 being disposed so as to cover at least a portion of the face gears 168 and 170, entanglement of sutures (threads) or the like in the face gears 168 and 170 can be prevented. In particular, the protective plate 171 has a shape that becomes narrower toward the rearward direction, and thus the protective plate 171 does not hinder movement in the yaw axis direction, and sutures or the like are not unnecessarily drawn into the face gears 168 and 170, or the gear 134, such that entanglement and interference therewith can more reliably be prevented.

The main axis member 128 is rotated in yawing directions about the first rotational axis Oy accompanying reciprocating movement of the wire 52, whereby the support bar 144 can make swinging movements in the XZ plane.

The tubular body 140, the gear body 126, and the gear body 130 are stacked together along the shaft 112, forming an axis thereof, and have a stacked height which is essentially equal to the height H, and thus are disposed with substantially no gaps between the pair of tongue-members 58.

The compound mechanism 102 further includes a drive base 150, a gear ring 152, a gear-attached pin 154, fastening nuts 156, 158, and a cover 160. The fastening nut 156 has a plurality of radial fine holes 156a defined therein for insertion of a narrow rotary tool. At least one of the fine holes 156a is exposed in a radial direction (see FIG. 3). The fastening nut 158 has parallel surfaces 158a, which are engageable by a rotary tool such as a wrench or the like.

The drive base 150 includes a tubular body 164 rotatably fitted over a proximal end portion of the support bar 144, a pair of support arms 166 projecting in the Z1 direction from both left and right ends of the tubular body 164, and a face gear 168 disposed on a surface of the tubular body 164 that faces the Z2 direction. Each of the support arms 166 serves to support the end effector 104, and has respective holes 166a defined therein, which are aligned in the X direction. After the tubular body 164 has been inserted onto the proximal end portion of the support bar 144, the fastening nut 156 is threaded over the externally threaded distal end portion of the support bar 144, whereby the drive base 150 is rotatably supported on the support bar 144 for rotation in rolling directions centrally about the support bar 144 (i.e., about the second rotational axis Or).

The face gear 168 is held in mesh with the gear 138. Consequently, the drive base 150 is rotatable about the second rotational axis Or, in response to rotation of the tubular body 136.

The gear ring 152 is in the form of a thin tubular body including a face gear 170 on a surface thereof facing the Z2 direction, and another face gear 172 on a surface thereof facing the Z1 direction. The gear ring 152 is fitted over the tubular body 164 of the drive base 150 for sliding rotation with respect to the outer circumferential surface of the tubular body 164. The gear ring 152 is fitted over the tubular body 164 such that the face gear 170 is slightly displaced off the face gear 168 of the drive base 150 in the Z1 direction, until being held in mesh with the gear 134. The face gear 170 meshes with the gear 134, such that the gear ring 152 is rotatable about the second rotational axis Or accompanying rotation of the gear body 126.

The gear-attached pin 154 includes a gear 174, which meshes with the face gear 172, and a pin 176 extending in the X1 direction from the center of the gear 174. The pin 176 has an externally threaded distal end portion. The pin 176 passes through the two holes 166a, such that the threaded distal end portion projects from one of the support arms 166, and the fastening nut 158 is threaded thereover. Owing thereto, the gear-attached pin 154, with the gear 174 meshing with the face gear 172, is rotatably supported with respect to the support arms 166. Further, the pin 176 is cut in a D-shaped cross section, for engagement with a portion of the end effector 104.

The cover 160 serves to protect the respective components of the compound mechanism 102 and the end effector 104, covering the gear ring 152 and the gear 174, etc. The cover 160 includes a tubular portion 180 extending in the Z2 direction, a pair of ears 182 that project in the Z1 direction from respective left and right end portions of the tubular portion 180, and slit-shaped holes 183 provided respectively in the ears 182. The ears 182 are shaped such that circumferential wall portions of the tubular portion 180 extend in the Z1 direction in gradually tapering conical shapes. The cover 160 has a lower portion fastened to a portion of the end effector 104 by a cover-fastening pin 162. The cover 160 has a diameter, which is equal to or smaller than the diameter of the connecting shaft 48 when viewed in front elevation. Holes 183 are provided over an area from the tubular portion 180 to the ears 182.

As made clear from FIG. 3, the compound mechanism 102 and the end effector 104 are formed with an elongated shape in the axial direction. The holes 183 are oblong holes in the lengthwise direction of the compound mechanism 102 and the end effector 104. Both ends of the holes 183 are formed in semicircular shapes.

The cover 160 may be in the form of a hollow cylindrical or conical-shaped cover for covering the compound mechanism 102 and the end effector 104, almost in their entirety, to such an extent that operations of the compound mechanism 102 and the end effector 104 will not be hampered. Further, the cover 160 may also be fastened using the pin 196.

By means of such a cover 160, foreign matter (body tissues, medical agents, sutures, etc.) can be prevented from entering inside the compound mechanism 102 and the end effector 104 making up the working unit.

Next, the end effector 104 comprises a first end effector member 190, a second end effector member 192, a link 194, and the pin 196. The pin 196 is aligned axially with the third rotational axis Og.

The first end effector member 190 includes a pair of laterally spaced side walls 200 facing each other and having respective holes 200a defined in distal end portions of the side walls 200 and respective holes 200b defined in rear end portions of the side walls 200, a first gripper 202 projecting in the Z1 direction from lower distal end portions of the side walls 200, and a cover mount 204 disposed on rear lower end portions of the side walls 200. The holes 200a have diameters such that the pin 196 can be press-fitted therein. The first gripper 202 narrows in width slightly along the Z1 direction and is formed with an arcuate distal end portion. The first gripper 202 has a number of small closely spaced conical upper projections disposed over the entire surface thereof substantially without gaps and facing in the Y1 direction.

The distal end portions of each of the side walls 200 are arcuate in shape, whereas both outer side surfaces of the rear end portions thereof have respective recesses 200c defined therein in which the support arms 166 are fitted. A hole 190a (see FIG. 5) is defined between the first gripper 202 and the cover mount 204 for preventing interference with respect to the rear end portion of the second end effector member 192. The cover mount 204 has a hole defined therein into which the cover-fastening pin 162 is press-fitted.

The second end effector member 192 comprises a base 210, a second gripper 212 extending in the Z1 direction from a distal end of the base 210, a pair of ears 214 extending in the Z2 direction from both left and right rear end portions of the base 210, and a shaft support sleeve 216 disposed on a lower surface at the distal end of the base 210. The shaft support sleeve 216 has a hole 216a defined therein, which has an inside diameter large enough to enable the pin 196 to be inserted therein. When the pin 196 is inserted into the shaft support sleeve 216 and is press-fitted, for example, in the hole 200a, the second end effector member 192 is made swingable centrally about the third rotational axis Og. The second gripper 212 is identical in shape to the first gripper 202, but is arranged in an upside-down orientation with respect to the first gripper 202. When the second end effector member 192 is rotated about the third rotational axis Og, the second gripper 212 is brought into abutment against the first gripper 202, so that a curved needle or the like can be gripped therebetween. The ears 214 have oblong holes 214a defined respectively therein.

The link 194 has a hole 220 defined in an end thereof and a pair of engaging fingers 222 disposed on the other end, which project laterally away from each other. The engaging fingers 222 slidably engage in the respective oblong holes 214a. The hole 220 is cut in a D-shaped cross section for receiving the pin 176 snugly therein, and thus, the hole 220 serves to position the pin 176 and prevent the pin 176 from rotating about its own axis. When the pin 176 is inserted in the holes 166a, as well as in the holes 200b and 220, the fastening nut 158 is threaded over the distal end portion of the pin 176, and the link 194 is made swingable about the pin 176.

Further, the wire 52 is wound for 1.5 turns around the tubular body 140, the wire 54 is wound 1.5 turns around the tubular body 136, and the wire 56 is wound 2.5 turns)(900° around the tubular body 116. As made clear from FIG. 5, the diameter of the tubular body 140 is set to a value equal to or greater than the sum of the diameter of the tubular body 116 and the diameters of the two wires 56. As viewed in plan, the wires 52, 54 are disposed slightly outwardly of the wire 56. Therefore, each of these wires is easily prevented from interfering with each other.

More specifically, the wire 56 is disposed inwardly of the wire 52, and the wire 56 does not interfere with the wire 52. Accordingly, without concern to the position of the wire 52, the wire 56 can be wound around the tubular body 116 over a region 116a thereof, which is about two-thirds of the overall height of the tubular body 116 (see FIG. 6). The region 116a is wide enough to allow the wire 56 to be wound 2.5 turns (or even more, e.g., 3.5 turns))(1260° therearound, so that the gear body 114 can be rotated to make 2.5 revolutions (or more). Further, since the rotation amount of the gear body 114 is large, the gear ratio between the gear 118 and the gear 134 can be set largely, thereby enabling an increase in the rotational torque of the gear body 126.

Figure 7:
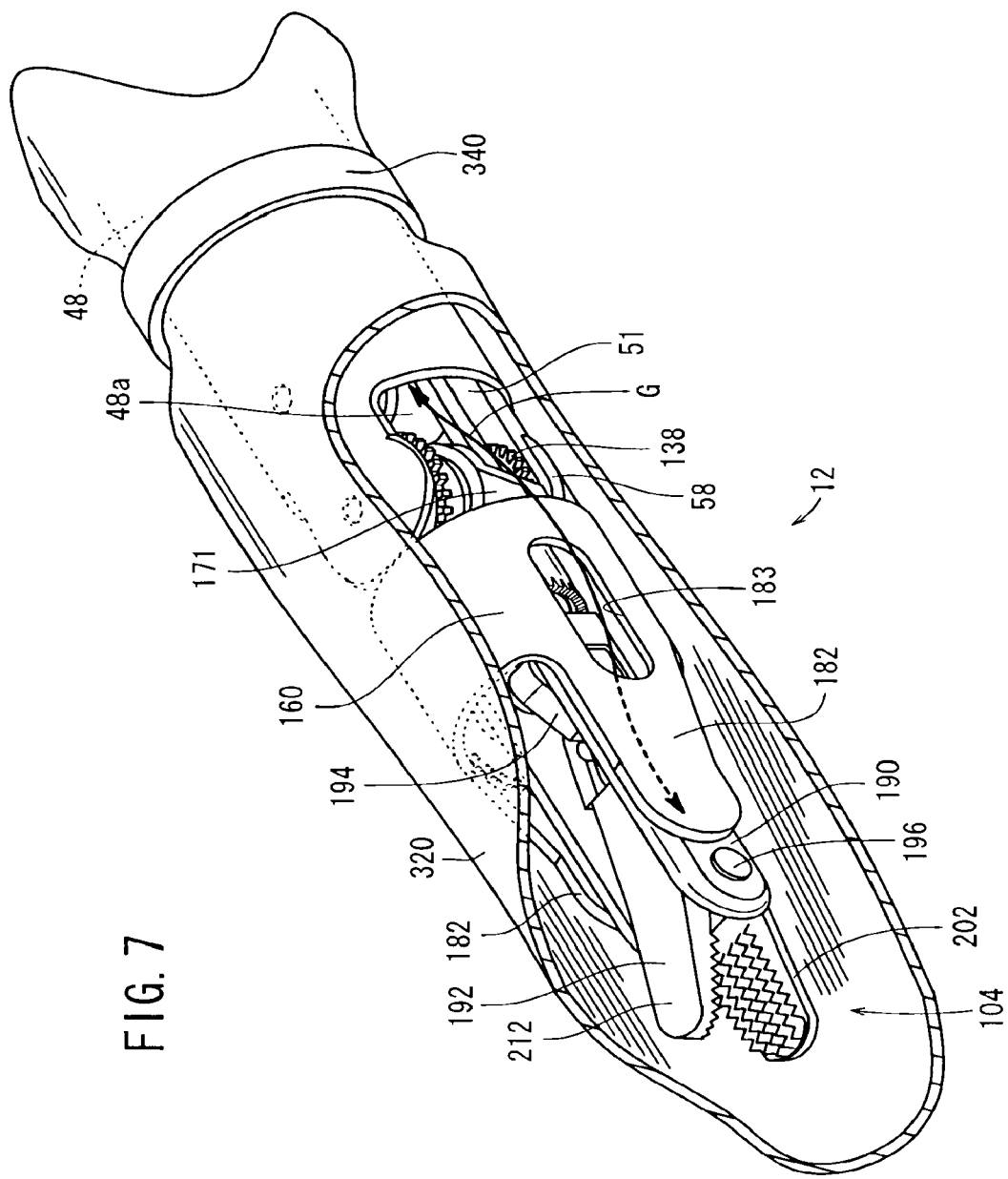
FIG. 7 is a view showing a condition in which a tube is connected to the distal end working unit for cleaning the same.
Figure 8:
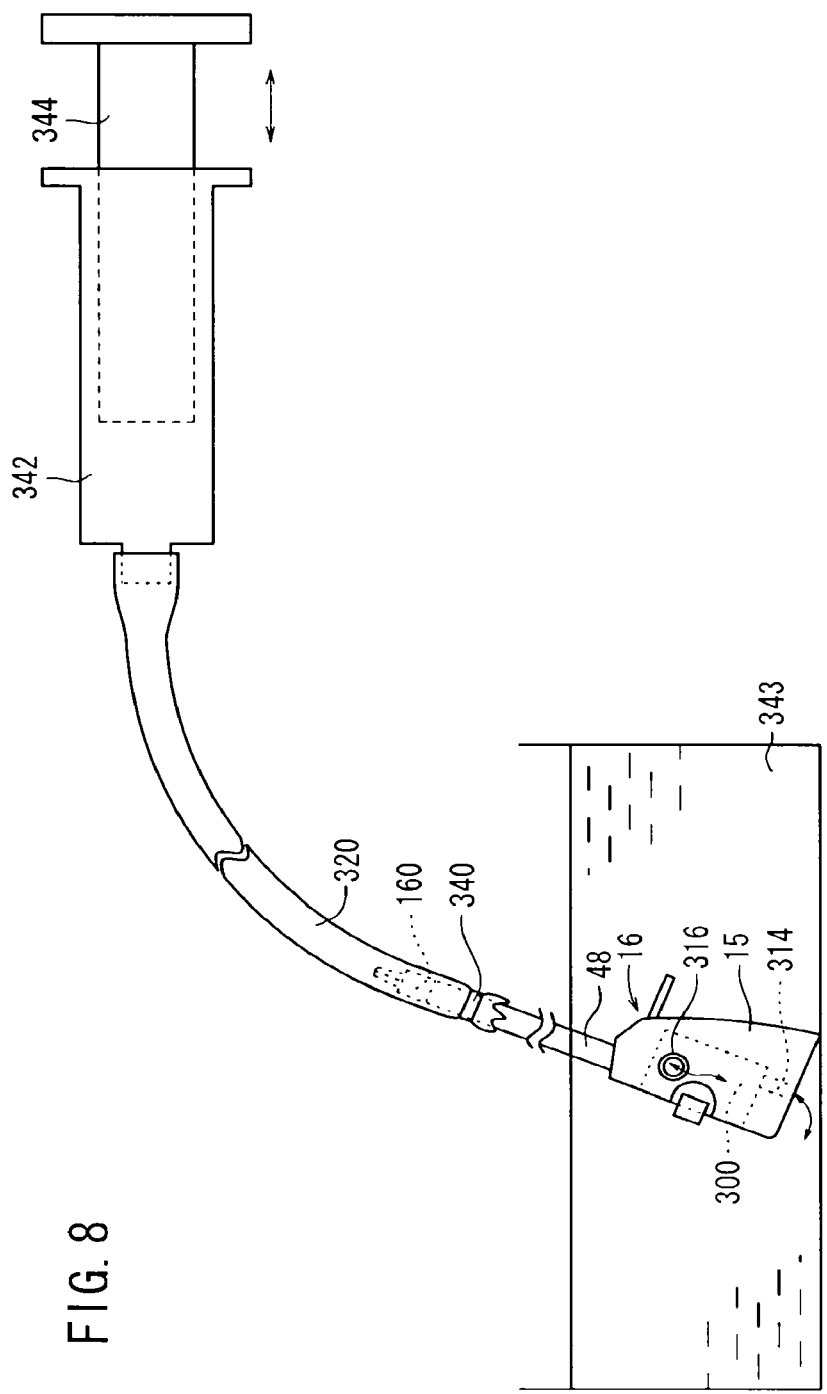
FIG. 8 is an explanatory drawing showing an aspect in which cleaning of the working unit is performed by a cleaning method according to an embodiment of the present invention.

Next, with reference to FIGS. 7 and 8, a description shall be given concerning a method for cleaning the working unit 16.

As shown in FIG. 7, after the working unit 16 is detached from the operation command unit 14, the distal end of the connecting shaft 48 along with the cover 160 is inserted into one end of a tube 320, and the tube 320 and connecting shaft 48 are sealed in a fluid-tight manner by a band (sealing means) 340. The tube 320 is appropriately larger in diameter than the connecting shaft 48 and the cover 160.

The sealing means is not limited to a band 340, and any means that provides a suitable fluid-tight seal may be used. Also, the seal need not strictly prohibit leakage of the cleaning agent. So long as the cleaning agent can flow through the connecting shaft 48 and the tube 320, a small amount of leakage can be tolerated.

Next, as shown in FIG. 8, the other end of the tube 320 is connected to a syringe (sucking and discharging means) 342, and an end of the connecting shaft 48, i.e., the connector 15, is immersed in the cleaning agent (which may be a water or an enzyme cleaning agent, for example), which is provided in a moderately-large vat 343. Initially, it is preferable to operate the piston 344 of the syringe 342 until the syringe 342 becomes filled with the cleaning agent. Preferably, the syringe 342 is chosen to have a sufficiently large capacity, which is greater than the total interior volume of the connecting shaft 48 and the tube 320.

Next, by reciprocally moving the piston 344, the cleaning agent is repeatedly sucked and discharged from the first cleaning hole 314 and/or the second cleaning hole 316 of the connector 15. The cleaning agent is drawn in from the first cleaning hole 314 and the second cleaning hole 316 and passes into the hollow space 48a of the connecting shaft 48, reaching the distal end working unit 12. During times of ordinary usage, the first cleaning hole 314 and the second cleaning hole 316 are blocked.

Incidentally, as clearly understood from FIG. 5, in the distal end working unit 12, the drive base 150 and the gear ring 152 are disposed therein, and the interior of the cover 160 is blocked almost entirely thereby, so that at first glance, a fluid passage does not appear to be formed thereby.

Notwithstanding, in the working unit 16, because the gap 51 is disposed between the cover 160 and the connecting shaft 48, and furthermore, owing to the holes 183 that are provided on both sides of the cover 160, as shown by the arrow G in FIG. 7, fluid flows through the gap 51 and the holes 183, so that a fluid passage is secured. The cleaning agent, which has passed through the gap 51 and the holes 183, flows through the tube 320 and is sucked inside the syringe 342. In the case of discharging the fluid, the fluid flows in reverse and passes from the syringe 342, through the tube 320, the holes 183, the gap 51, and the connecting shaft 48, whereupon the cleaning agent is discharged into the vat 343. The discharged cleaning agent is diluted with the remaining cleaning agent in the vat 343, so that when sucked again in the next cycle, a cleaning agent having adequate purity can be drawn in.

In accordance with such a cleaning method, by continual reciprocating movements of the piston 344 in the syringe 342, the cleaning agent is sucked and discharged through the hollow space 48a of the connecting shaft 48, and without blockage of the flow passage midway by mechanical components, the cleaning agent flows through the gap 51 and the holes 183, whereby cleaning can easily be performed. Further, the connecting shaft 48 and the distal end working unit 12 can be cleaned easily and highly effectively at the same time.

As a cleaning method for the distal end working unit 12, the tube 320 may be arranged such that the tube 320 covering the cover 160 only, wherein the cleaning agent is made to flow through the tube 320 from the other end thereof. Consequently, the cleaning agent is made to flow sideways from the holes 183 of the cover 160, producing multiple flows of the cleaning agent inside the cover 160, whereby the end effector 104 and the compound mechanism 102 can be cleaned effectively. Further, a cleaning means such as a brush or the like may be used for cleaning inside of the cover 160.

Because holes 183 are disposed on both left and right sides of the cover 160, cleaning on the left and right sides of the end effector 104 can also be carried out. Since the holes 183 are formed with semicircular shapes at the end portions thereof, it is unlikely that sutures (threads) and the like, which are used for suturing during surgery, will become caught thereon and drawn into the interior of the end effector 104.

A cleaning means, such as a brush, a high-pressure water flow means, or means for supplying compressed air or the like may be inserted from the holes 183, whereby cleaning is carried out thereby.

Further, even when a structure is provided for operating the piston 344 automatically so as to be reciprocally moved over a long period of time, only the cleaning agent provided in the vat 343 is utilized, so that a large amount of cleaning agent is not consumed inadvertently. The used cleaning agent is collected into the vat 343 without scattering or spillage of the cleaning agent, so that no special anti-scattering means or collecting means is required, and disposal processing of the cleaning agent can be easily performed. The fluid suction and discharge means is not limited to the syringe 342. For example, an automatically driven cylinder or the like may be used in place of the syringe 342.

With the above-mentioned compound mechanism 102, through rotation of the gear body 130, rotation is transmitted from the gear 138 to the face gear 168, whereby the drive base 150, and the end effector 104 coupled to the drive base 150, can be rotated about the second rotational axis Or. Further, by rotation of the gear body 114, rotation is transmitted from the gear 118 to the pin 176 through the gear 134, the face gear 170, the face gear 172 and the gear 174, thereby enabling the gear-attached pin 154 to be rotated.

As described above, with the distal end working unit 12, in the manipulator 10 according to the present embodiment, as a result of providing the cover 160, foreign matter can be prevented from entering into the distal end working unit 12. In addition, a cleaning agent can be injected from the holes 183 formed in side surfaces of the cover 160, whereby cleaning of the distal end working unit 12 can be carried out.

A tube 320 that is appropriately large in diameter is used to cover the connecting shaft 48 and the cover 160, and by causing reciprocal movement of the piston 344 in the syringe 342, the cleaning agent is sucked in and discharged through the hollow space 48a of the connecting shaft. Without blockage of the fluid passage by mechanical components, the cleaning agent flows through the gap 51 and the holes 183, so that cleaning can be carried out easily and effectively.

The cover 160 is connected to the motive force transmitting member (wires) and is moved together with movements of the distal end working unit 12. For example, when yaw-axis movements of the distal end working unit 12 take place, the cover 160 also is moved around the yaw-axis with respect to the connecting shaft 48.

Due to the existence of the gap 51 between the connecting shaft 48 and the cover 160, the exposed region of the yaw axis joint becomes widened by movement of the yaw axis, whereby the effectiveness of cleaning can be enhanced.

Holes 183 are provided not only on the tubular portion 180, but also over an area from the tubular portion 180 to the ears 182, i.e., formed as an elongate slit in the Z direction. Accordingly, the cover 160 has strength higher than a cover in which holes having the same size are provided only on the tubular portion 180. Further, flow of the cleaning agent through the holes 183 in the Z1 or Z2 direction is prevented from being blocked, and thus, cleaning efficiency is improved.

Further, from the fact that the cover 160 is connected to the motive force transmitting member, the distal end working unit 12, which is connected to the motive force transmitting member, can be covered efficiently, and compared to a situation in which the cover 160 is attached to the connecting shaft 48 and covers the distal end working unit 12, a more compact cover shape results, which does not cause an obstruction to operation of the manipulator.

When holes 183 are disposed in the cover 160, apart from the aforementioned cleaning method using flowing water, a method in which the flowing water flows effectively by a washer-disinfector apparatus, or a method in which a cavitation effect is developed in detail by means of an ultrasonic cleaning apparatus, can be utilized.

Further, in processes involving plasma sterilization or EOG (ethylene oxide gas) sterilization as well, contact with the sterilizing environment increases, so that more effective processing can be carried out.

The holes 183 are disposed substantially centrally on left and right side surfaces of the cover 160. At this location, the possibility of direct contact with living tissue inside the body cavity is minimized. Therefore, it is unlikely that foreign substances from living body tissue will enter the driving section that moves relatively, including the gears, the links, and the like disposed inside the cover 160.

Figure 9:
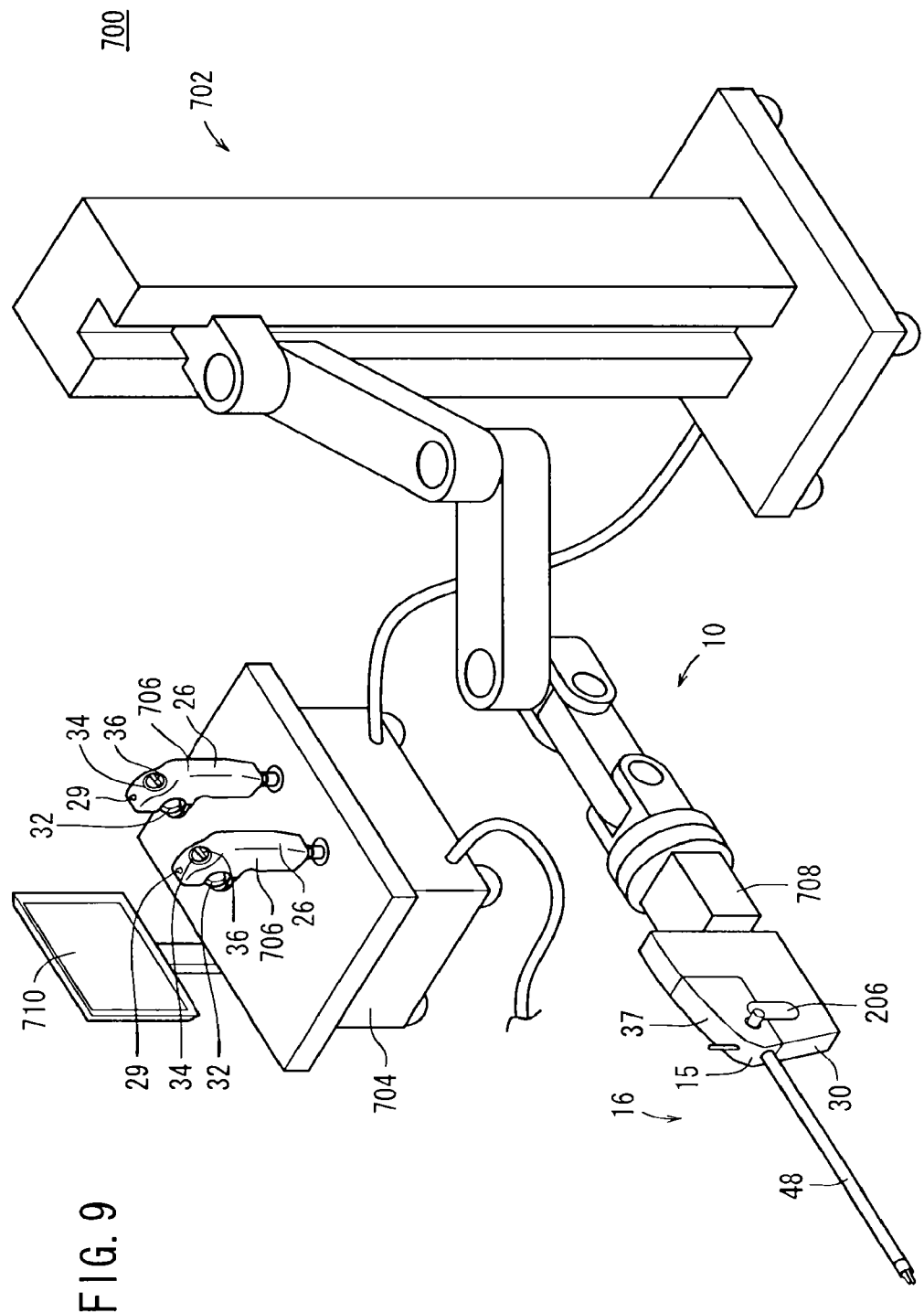
FIG. 9 is an outline perspective view of a surgical robot system in which the working unit is connected to an end of a robot arm.

The working unit 16 has been described as being connected to an operation command unit 14, which is operated manually. However, as shown in FIG. 9, the working unit 16 may also be applied to a surgical robot system 700.

The surgical robot system 700 includes a multi-articulated robot arm 702 together with a console 704. The working unit 16 is connected to an end of the robot arm 702. The same mechanism as that of the aforementioned actuator block 30 is provided at the end of the robot arm 702, thereby enabling connection and driving of the working unit 16. In this case, the manipulator 10 is made up from the robot arm 702 and the working unit 16. The robot arm 702 may comprise means therein for causing movements of the working unit 16, and is not limited to a stationary system, but for example, may also be an autonomous mobile system. For the console 704, a table type structure or a control panel structure may be adopted.

When the robot arm 702 includes six or more independent joints (rotational or slide axes), the position and orientation of the working unit 16 can be set arbitrarily in an appropriate manner. An end actuator block 30 may be constructed integrally with an end portion 708 of the robot arm 702.

The robot arm 702 is moved under operations of the console 704, and may be configured to move automatically according to a given program, or to move correspondingly to movements of a joystick 706 disposed on the console 704, or by a combination of such operations. The console 704 includes the functions of the aforementioned controller 45.

Two joysticks 706 and a monitor 710 are provided on the console 704, serving as an operation command section for mechanisms among those of the aforementioned operation command unit 14 excluding the actuator block 30. Although not shown by the present illustration, two robot arms 702 may be provided, which are operated separately by two joysticks 706. The two joysticks 706 are disposed at positions where they can be easily operated by both hands. The monitor 710 displays information of images or the like produced by an endoscope.

The joysticks 706 are capable of being moved up and down, left and right, and of making twisting or torsional movements, as well as tilting movements, wherein the robot arm 702 can be moved responsive to the movements of the joysticks 706. Further, by the trigger lever 32, the first command lever 34, and the second command lever 36 which are provided on the grip handle 26, the same operations as with the operation command unit 14 are possible. The joysticks 706 may also comprise a master arm. The communication means between the robot arm 702 and the console 704 may consist of wired or wireless communications, communication over a network, or any combination of the same.

The working mechanism for a medical manipulator and the cleaning method according to the present invention are not limited to the aforementioned embodiments. It should be understood that various other configurations may be adopted without deviating from the scope of the invention as set forth in the appended claims.

What is claimed is:

1. A cleaning method for a working mechanism for a medical manipulator, wherein the working mechanism of the medical manipulator comprises:

a hollow shaft;
a motive force transmitting member disposed in the shaft;
a working unit disposed at one end of the shaft and equipped with a distal end working unit, which is moved by the motive force transmitting member; and
a cover that covers at least a portion of the distal end working unit,
wherein a gap is provided between the cover and the shaft, and
at least one hole is disposed laterally on a side of the cover, the cleaning method comprising the steps of:
inserting an end of the shaft together with the cover into one end of a tube;
sealing the tube and the shaft with a sealing element;
disposing a sucking and discharging element on another end of the tube; and
immersing another end of the shaft into a cleaning agent,
wherein, by activating the sucking and discharging element, sucking and discharging of the cleaning agent is carried out repeatedly, from the other end of the shaft.

2. The method according to claim 1, wherein the at least one hole is formed as an elongated slit in a longitudinal direction of the working unit.

3. The method according to claim 2, wherein both ends of the at least one hole have semicircular shapes.

4. The method according to claim 1, wherein the cover includes a tubular portion on a proximal end side thereof, and a pair of ears which project from sides of the tubular portion toward a distal end of the cover, and
the at least one hole is provided over an area from the tubular portion to the ear.

5. The method according to claim 1, wherein the cover is movable with respect to the shaft together with the distal end working unit.

6. The method according to claim 1, wherein the gap is partially exposing the motive force transmitting member and communicating with a hollow space of the shaft.

7. The method according to claim 1, wherein the at least one hole is partially exposing a driving part of the distal end working unit which is disposed in the interior of the cover.

8. The method according to claim 1, wherein the at least one hole, the gap, and the hollow space define a flow path, and
the distal end working unit can be cleaned by flow of the cleaning agent through the flow path.

9. The method according to claim 1, wherein the sucking and discharging element is a syringe.

10. The method according to claim 1, wherein the cleaning agent is water.

11. The method according to claim 1, wherein the at least one hole includes a plurality of holes.

12. A cleaning method for a working mechanism for a medical manipulator, wherein the working mechanism of the medical manipulator comprises:
a hollow shaft;
a motive force transmitting member disposed in the shaft;
a working unit disposed at one end of the shaft and equipped with a distal end working unit, which is moved by the motive force transmitting member; and
a cover that covers at least a portion of the distal end working unit and is movable with respect to the shaft together with the distal end working unit,
wherein a gap is provided between the cover and the shaft, the gap partially exposing the motive force transmitting member and communicating with a hollow space of the shaft,
holes are disposed laterally on both sides of the cover, the holes partially exposing a driving part of the distal end working unit which is disposed in the interior of the cover, and
the holes, the gap, and the hollow space defining a flow path, wherein the distal end working unit can be cleaned by flow of a cleaning solution through the flow path,
the cleaning method comprising the steps of:
inserting an end of the shaft together with the cover into one end of a tube;
sealing the tube and the shaft with a sealing element;
disposing a sucking and discharging element on another end of the tube; and
immersing another end of the shaft into a cleaning agent,
wherein, by activating the sucking and discharging element, sucking and discharging of the cleaning agent is carried out, from the other end of the shaft.

13. The method according to claim 12, wherein each of the holes is formed as an elongated slit in a longitudinal direction of the working unit.

14. The method according to claim 13, wherein both ends of each of the holes have semicircular shapes.

15. The method according to claim 12, wherein the cover includes a tubular portion on a proximal end side thereof, and a pair of ears which project from sides of the tubular portion toward a distal end of the cover, and
the holes are provided over an area from the tubular portion to the ear.

16. The method according to claim 12, wherein the sucking and discharging element is a syringe.

17. The method according to claim 12, wherein the cleaning agent is water.

* * * * *